United States Patent [19]

Urakawa et al.

[11] 4,048,014

[45] Sept. 13, 1977

[54] METHOD FOR OBTAINING UROKINASE

[75] Inventors: Masaharu Urakawa; Hiroshi Sumiyama, both of Hitachi, Japan

[73] Assignee: Hitachi Chemical Company, Ltd., Tokyo, Japan

[21] Appl. No.: 702,900

[22] Filed: July 6, 1976

[30] Foreign Application Priority Data

July 16, 1975 Japan .................................. 50-86765

[51] Int. Cl.$^2$ ............................................ C07G 7/026
[52] U.S. Cl. .................................................. 195/66 B
[58] Field of Search ............................ 195/66 B, 66 R

[56] References Cited

U.S. PATENT DOCUMENTS 3,723,252  3/1973  Ogawa et al. ..................... 195/66 B

OTHER PUBLICATIONS

Bergstrom, Arkiv for Kemi, vol. 21, No. 48, pp. 535–546, 1963.

Primary Examiner—Lionel M. Shapiro
Attorney, Agent, or Firm—Flynn & Frishauf

[57] ABSTRACT

A method for obtaining urokinase which comprises steps of contacting a partially purified urokinase-containing solution with diatomaceous earth at a pH range of 4.0 – 8.0, washing said diatomaceous earth adsorbing urokinase thereon with a buffer solution of pH 6.5 – 9.0 and eluting the urokinase from the adsorbate.

6 Claims, No Drawings

METHOD FOR OBTAINING UROKINASE

This invention relates to a method for obtaining urokinase. More particularly, this invention relates to a concentrating and purifying method for obtaining urokinase of high purity in high yield from a partially purified urokinase-containing solution. Urokinase is an enzyme which converts plasminogen into plasmin. Since urokinase can lyse a blood clot produced in a blood vessel when injected into human body, it is attracting attention as a remedy of thromboembolis or an auxiliary agent for a cartinostatic agent. Urokinase is present in human urine in extremely low concentration. It is reported that the urine excreted by a female in 24 hours contains 5,770 ± 1,420 units and the urine by a male in 24 hours contains 6,800 ± 1,520 units. Various methods for obtaining urokinase from human urine have been reported, in which heavy metals, silica gel or various kinds of ion-exchange resin are employed.

This invention relates to a method for obtaining urokinase, which method is superior to the conventional arts with respect to the yield and the specific activity of the urokinase obtained. A similar art to the present invention was reported by Kurt Bergstrom in Arkiv. For Kemi Bd 21, nr. 48, 535 – 546. According to this report, urokinase having 500 – 800 ploug units/mg (corresponding to 750 – 1,200 international units (abbreviated as IU hereinafter)) of specific activity could be obtaining by contacting urine with Hyflo Super Cel (manufactured by Johns Manville Sales Corp.) at pH 5.0, washing the adsorbate with water sufficiently, salting out with a 85%-saturated solution of ammonium sulfate, dissolving the salted-out substances in a small amount of water, subjecting the solution thus obtained to isoelectric precipitation, dissolving the precipitate thus obtained in water and lyophilizing the solution. 4,000 ploug units (corresponding to 6,000 IU) of urokinase was recovered from 1 l of a starting urine.

The present invention provides a method for obtaining urokinase which is superior to such a method as the above method with respect to the yield and the specific activity of the urokinase obtained. Namely, this invention relates to a method for obtaining urokinase which comprises contacting a partially purified urokinase-containing solution with diatomaceous earth at a pH range of 4.0 – 8.0, then washing the adsorbate with a buffer solution of pH 6.5 – 9.0 and eluting the urokinase from the adsorbate. In the present invention, the partially purified urokinase-containing solution means the following solutions: for example, a urokinase-containing solution obtained by adjusting the pH of human urine to above 7.5 with such basic solutions as that of sodium hydroxide, potassium hydroxide, ammonia, etc. and then centrifuging to remove the precipitates thus produced; a urokinase-containing solution obtained by the treatment of human urine according to the present method; and urokinase-containing solutions by purifying human urine according to other publicly known methods. When human urine is adjusted to pH above 7.5 with a basic solution, precipitates of proteins are produced and can be removed effectively from the solution. It is unfavorable to bring the pH value of the urokinase-containing solution to above 9.0, since, at a pH above 9.0, the removal effect of the precipitates of proteins is not increased and urokinase is liable to be deactivated. A partially purified urokinase-containing solution is adjusted to pH 4.0 – 8.0 and then contacted with diatomaceous earth. The contacting operation may be conducted either by mixing said solution with diatomaceous earth with stirring (batch method) or by making said solution flow through a column filled with diatomaceous earth (column method). In the case of the batch method, adjustment of the pH value may be carried out either before or after the contacting operation. In the case of the column method, the pH value should necessarily be adjusted prior to the contacting operation. At a pH value below 4.0, precipitates are produced and urokinase is difficult to absorb, and at a pH above 8.0, urokinase is easily deactivated. So an operation under a pH below 4.0 or above 8.0 is unfavorable for the purpose. Urokinase of excellent specific activity can be recovered in high yield by adjusting the pH value of the solution to 5.0 – 7.0. Particularly, pH values of 6.0 – 6.5 give the most excellent results.

The adjustment of the pH value is conducted with such protonic acids as sulfuric acid, hydrochloric acid, oxalic acid and so on, and such buffer solutions as phosphate buffer solutions.

As a diatomaceous earth, Celite 503, Celite 535, Celite 545, Celite 560 and Hyflo Super Cel (all are trademarks of Johns Manville Sales Corp.) can be employed. This diatomaceous earth may preferably be used in an amount of above 2 g. per 1 l of the above mentioned solution, particularly above 10 g./l to obtain urokinase in high total yield. The contacting time of the solution with diatomaceous earth is not limited, but preferably is above 10 minutes, particularly above 20 minutes.

Then, the diatomaceous earth adsorbing urokinase is washed with such buffer solutions as a phosphate buffer solution of pH 6.5 – 9.0. When the pH value is out of the range of from 6.5 to 9.0, urokinase cannot be obtained in such yield and purity as will be described hereinafter. Preferably, the pH value is at a range of from 7.5 to 8.5 and the ionic strength is at a range of from 0.1 to 1.5 (for example, 0.1 or 0.2 M phosphate buffer solution of pH 7.5). The amount of the washing solution may preferably be, in the case of the washing of a column, 10 times the volume of the diatomaceous earth in the column. Proteins other than urokinase are removed to a great extent by this washing procedure.

After washing the adsorbate, urokinase adsorbed by diatomaceous earth is eluted out. The elution is conducted with such alkaline solutions as aqueous ammonia and an aqueous solution of sodium carbonate. It is particularly preferred to use an aqueous ammonia of above 4 % concentration in order to obtain urokinase in good total yield.

The urokinase-containing solution thus obtained is neutralized with an acid and concentrated by such conventional arts as salting out with above 50%-saturated, particularly with a 55 – 65 %-saturated solution of ammonium sulfate, lyophilization, ultrafiltration, isoelectric precipitation, and precipitation method with alcohol.

According to the present procedure described above, urokinase of 6,000 – 7,000 IU/mg of specific activity can be recovered from human urine, the recovery being 7,500 IU per 1 l urine. The specific activity and the recovery by the present method are very high.

When the solution thus concentrated is subjected further to the present processes (adsorption with diatomaceous earth and so on) repeatedly, more effective results can be obtained.

This invention will further be illustrated by the following non-limitative examples.

EXAMPLE 1

100 l of urine was adjusted to pH 8.5 with a 40 % aqueous solution of sodium hydroxide. After removal of the resulting precipitates, the solution obtained was adjusted to pH 6.0 with 9 N- sulfuric acid. To this solution 1 Kg of Hyflo Super Cel was added and contacted with the solution with stirring for 30 minutes. Thereafter, the Hyflo Super Cel adsorbing urokinase was filled in a column. Then the adsorbate was sufficiently washed with a 0.1 M-phosphate buffer solution (about 40 l) of pH 8.0 and eluted out with a 4 % aqueous ammonia. The eluate is neutralized to pH 7.0 with 9 N-sulfuric acid. After removing the precipitates produced with a centrifuge, the solution obtained was 60 %-saturated by adding ammonium sulfate. After standing at 4° C overnight, the substance salted out was collected and dissolved in 50 ml of distilled water. The solution was again subjected to centrifugation to remove the insoluble substances and the filtrate thus obtained was dialyzed at 4° C overnight and lyophilyzed to give urokinase. Total yield: $7.5 \times 10^5$ IU. Specific activity: 6,700 IU/mg.

EXAMPLE 2

100 l of urine was adjusted to pH 8.5 with a 40 % aqueous solution of sodium hydroxide. After removal of the precipitates produced, the solution was adjusted to pH 6.0 with 9N-sulfuric acid. After adding 1 Kg of Celite 535 and stirring for 30 minutes, the Celite was collected and filled in a column. After washing the adsorbate with a 0.1 M phosphate buffer solution (about 40 l) of pH 7.5, elution was conducted with a 4 % aqueous ammonia. After neutralizing the eluate with 9N-sulfuric acid, the insoluble precipitates produced were removed by using a centrifuge. Ammonium sulfate was added to this solution to make it 60 %-saturated. After standing at 4° C overnight, the substances salted out were collected and dissolved in 50 ml of distilled water. The solution was again subjected to centrifugation to remove insoluble precipitates. After dialyzing the filtrate at 4° C overnight, the dialyzed solution was lyophilyzed to give urokinase of 6,900 IU/mg of specific activity in a yield of $8.0 \times 10^5$ IU.

EXAMPLE 3

The concentrate obtained in Example 2. by salting out with ammonium sulfate was made to flow through the column packed with 270 ml of Celite 545. After the adsorbate was washed sufficiently with a 0.1 M phosphate buffer solution of pH 7.5 (about 3 l), urokinase was eluted out with a 4 % aqueous ammonia. After neutralization of the eluate, insoluble substances were removed by using a centrifuge. The solution thus obtained was dialyzed overnight and lyophilyzed to give urokinase of 26,000 IU/mg of specific activity in a total yield of $7.3 \times 10^5$ IU.

REFERENTIAL EXAMPLE 1

According to the procedure of Example 1, but washing was conducted by substituting a deionized water of pH 5.0 for the buffer solution, urokinase of 1,500 IU/mg of specific activity was obtained in a total yield of 800,000 IU.

REFERENTIAL EXAMPLE 2

According to the procedure of Example 1, but washing of the diatomaceous earth was conducted with a saline solution of pH 5.0 of the buffer solution, urokinase of 2,000 IU/mg of specific activity was obtained in a total yield of 790,000 IU.

What is claimed is:

1. A method for obtaining urokinase which comprises contacting a partially purified urokinase-containing solution with diatomaceous earth at a pH range of 4.0 - 8.0, washing said diatomaceous earth adsorbing urokinase thereon with a buffer solution of pH 6.5 - 9.0 and eluting the urokinase from the adsorbate with a basic solution.

2. A method as claimed in claim 1, wherein said partially purified urokinase-containing solution is obtained by removing the precipitates produced by adjusting the pH of human urine to above 7.5 with a basic solution.

3. A method as claimed in claim 1, wherein said contact operation is carried out at a pH range of 5.0 - 7.0 and said washing operation is carried out with a buffer solution of pH 7.5 - 8.5.

4. A method as claimed in claim 1, wherein said buffer solution of pH 6.5 -9.5 is a phosphate buffer solution.

5. A method as claimed in claim 1, wherein said basic solution is an aqueous solution of ammonia or sodium carbonate.

6. A method as claimed in claim 5, wherein said aqueous solution of ammonia is an aqueous solution containing above 4 % of ammonia.

* * * * *